United States Patent [19]

Ward

[11] Patent Number: 4,959,375
[45] Date of Patent: Sep. 25, 1990

[54] PIPERIDINE DERIVATIVES USEFUL AS 5-HT₃ ANTAGONISTS

[75] Inventor: Terence J. Ward, Maidenhead, England

[73] Assignee: John Wyeth & Brothers Limited, Maidenhead, England

[21] Appl. No.: 313,104

[22] Filed: Feb. 21, 1989

[30] Foreign Application Priority Data

Mar. 3, 1988 [GB] United Kingdom ................ 8805064

[51] Int. Cl.⁵ .................. A61K 31/445; C07D 211/98
[52] U.S. Cl. .................................... 514/323; 514/316; 546/187; 546/199; 546/200; 546/201
[58] Field of Search ............... 546/187, 199, 201, 200; 514/316, 323

[56] References Cited

U.S. PATENT DOCUMENTS 4,758,668 7/1988 Strupczewski ................ 546/199

OTHER PUBLICATIONS

Irikura et al., J. Med. Chem. 14, 357–361 (1971).

Primary Examiner—Mary C. Lee
Assistant Examiner—Jacqueline Haley
Attorney, Agent, or Firm—Arthur G. Seifert

[57] ABSTRACT

Piperidine derivatives of the formula

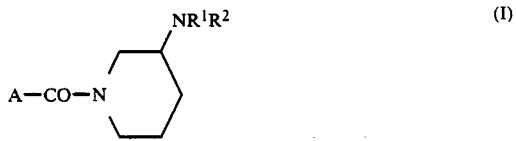

and pharmaceutically acceptable acid addition salts thereof wherein A represents an aromatic radical selected from

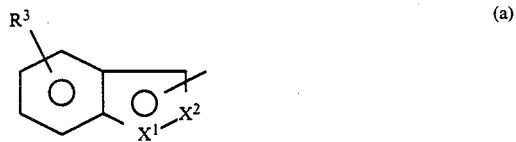

wherein $R^3$ is hydrogen, $(C_{1-4})$alkyl, $(C_{1-4})$alkoxy or halogen; $X^1$-$X^2$ represents $CH_2$—CH, $NR^4$—CH, O—CH, S—CH, $CH_2$—N, O—N, S—N, $NR^4$—N, CH—$NR^4$ or N—$NR^4$ [where $R^4$ is hydrogen, $(C_{1-4})$alkyl, phenyl or phenyl$(C_{1-4})$alkyl] or

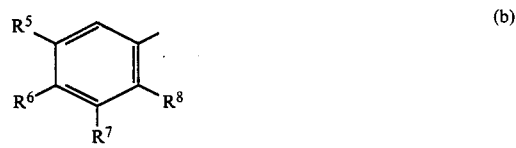

wherein $R^5$, $R^6$, $R^7$ and $R^8$ are independently hydrogen, halogen, trifluoromethyl, $(C_{1-4})$alkyl, $(C_{1-4})$alkoxy, hydroxy, nitro, amino, $(C_{1-4})$alkylamino, di$(C_{1-4})$alkylamino, $(C_{2-4})$alkanoylamino, mercapto or $(C_{1-4})$alkylthio and $R^1$ and $R^2$ are independently hydrogen, $(C_{1-4})$alkyl or $(C_{1-4})$alkylphenyl or $R^1$ and $R^2$ together with the nitrogen atom to which they are attached represent pyrrolidino or piperidino possess 5-HT₃-antagonistic activity.

11 Claims, No Drawings

PIPERIDINE DERIVATIVES USEFUL AS 5-HT₃ ANTAGONISTS

This invention relates to piperidine derivatives. In particular the invention relates to piperidine derivatives for use as 5-HT$_3$-antagonists, pharmaceutical preparations containing the piperidine derivatives, certain novel piperidine derivatives and processes for preparing them.

The invention particularly relates to piperidine derivatives of the formula

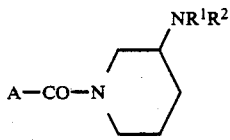

and pharmaceutically acceptable acid addition salts thereof, wherein A represents an aromatic radical selected from

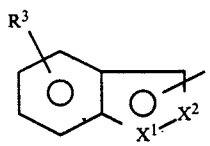

wherein $R^3$ is hydrogen, $(C_{1-4})$alkyl, $(C_{1-4})$alkoxy or halogen; $X^1$—$X^2$ represents $CH_2$—CH, $NR^4$—CH, O—CH, S—CH, $CH_2$—$N$, $O$—$N$, $S$—$N$, $NR^4$—$N$, CH—$NR^4$ or N—$NR^4$ [where $R^4$ is hydrogen, $(C_{1-4})$alkyl, phenyl or phenyl$(C_{1-4})$alkyl] or

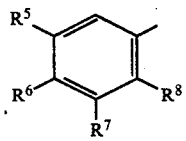

wherein $R^5$, $R^6$, $R^7$ and $R^8$ are independently hydrogen, halogen, trifluoromethyl, $(C_{1-4})$alkyl, $(C_{1-4})$alkoxy, hydroxy, nitro, amino, $(C_{1-4})$alkylamino, di$(C_{1-4})$alkyl-amino, $(C_{2-4})$alkanoylamino, mercapto or $(C_{1-4})$alkylthio and $R^1$ and $R^2$ are independently hydrogen, $(C_{1-4})$alkyl or $(C_{1-4})$alkylphenyl or $R^1$ and $R^2$ together with the nitrogen atom to which they are attached represent pyrrolidino or piperidino.

The above mentioned piperidine derivatives possess 5-HT$_3$-antagonistic activity, as more fully explained below. Accordingly the present invention provides a piperidine derivative of formula (I) as defined above or a pharmaceutically acceptable acid addition salt thereof for use in antagonising 5 HT$_3$ receptors in a mammal. In another aspect the invention provides a pharmaceutical composition for use in antagonising 5-HT$_3$ receptors in a mammal comprising a piperidine derivative of formula (I) as defined above or a pharmaceutically acceptable acid addition salt thereof in association with a pharmaceutically acceptable carrier.

Most of the compounds of formula (I) are novel and accordingly, in another aspect, the present invention provides piperidine derivatives of formula (I) above or the pharmaceutically acceptable acid addition salts thereof, with the proviso that when A represents 3,4,5-trimethoxyphenyl $R^1$ and $R^2$ are not both hydrogen. The compound of formula (I) in which A represents 3,4,5 trimethoxyphenyl and $R^1$ and $R^2$ are both hydrogen is described by T. Irikura et al, J.Med Chem., 1971, 14, 357–361 as an intermediate for compounds tested for antiulcer activity.

Where in this specification a radical is referred to as "$(C_{1-4})$alkyl" the radical may be straight chain or branched and may be methyl, ethyl, propyl or butyl. A $(C_{1-4})$alkoxy group may also be straight chain or branched and may be methoxy, ethoxy, propoxy or butoxy. A $(C_{2-4})$alkanoyl group may be acetyl, propionyl or butyryl. A halogen radical is preferably chlorine or fluorine.

When A has the meaning (a), $X^1$—$X^2$ is preferably $NR^4$—CH or $NR^4$—N. $R^4$ is preferably hydrogen or $(C_{1-4})$alkyl. $R^3$ is preferably hydrogen.

When A has the meaning (b) a particularly preferred meaning for A is 3,5-dichlorophenyl.

The compounds of the invention are amide derivatives and may be prepared by methods known for the preparation of amides. For example an appropriate acid of formula (II)

A—COOH  (II)

(wherein A has the meaning given above) or a reactive derivative thereof or a precursor of the acid or reactive derivative may be coupled with an appropriate amine of formula (III)

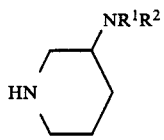

(wherein $R^1$ and $R^2$ have the meanings given above) or a precursor thereof. The coupling is preferably carried out by the "carboxyl activation" coupling procedure. Descriptions of carboxyl activating groups are found in general textbooks of peptide chemistry. Examples of the activated carboxyl group are the acid chloride, acid bromide, anhydride, azide, imidazolide (obtained from carbonyldiimidazole), activated ester (eg. 1-benzotriazolyl, 2,4,5 trichlorophenyl or succinimido activated esters) or 0-acyl urea obtained from a dialkylcarbodiimide eg. dicyclohexylcarbodiimide (DCC). If either the activated acid or the amine contains a group that would interfere with the reaction a precursor of the desired compound may be employed in the reaction in which the group is protected and the protecting group may be removed subsequently. For example if it is desired to prepare a compound of formula (I) in which $R^1$ and/or $R^2$ is hydrogen a precursor of the amine of formula (III may be used in which the primary and secondary amine group —$NR^1R^2$ is protected (eg with a benzyl group) and the protecting group is removed after the coupling has occurred. Another example of a precursor of the amine (III) is a piperidone of formula

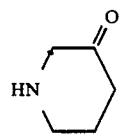

This may be coupled with a reactive derivative of the acid (III) and the resulting compound

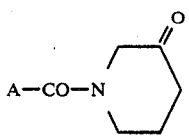
(V)

subjected to reductive amination (eg. with an amine of formula $R^1R^2NH$ and a reducing agent such as sodium cyanoborohydride, or other hydride reducing agents eg. sodium borohydride). Alternatively the ketone (V) may be converted to the oxime with hydroxylamine and the oxime reduced (eg. by catalytic hydrogenation with, for example, hydrogen/platinum or by sodium/alcohol) to give the primary amine of formula (I) in which both $R^1$ and $R^2$ are hydrogen.

The compounds of the invention may be converted into other compounds of the invention eg. in a conventional manner. For example a compound of formula (I) in which $R^1$ and $R^2$ are both hydrogen may be alkylated or alkylphenylated (eg. benzylated) to give a compound in which $R^1$ and/or $R^2$ is $(C_{1-4})$alkyl or $(C_{1-4})$-alkylphenyl.

The starting materials for the above processes are either described in the literature or may be prepared by methods known for analogous compounds.

If in the processes described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the present invention possess pharmacological activity. In particular they antagonise specific 5 hydroxytryptamine (5-HT) receptors in warm blooded animals. Specifically the compounds possess 5-HT3 antagonistic activity and hence are of value in conditions where antagonism of 5-HT3 receptors is desirable. 5-HT3 antagonists are also termed "antagonists of "neuronal" 5-hydroxytryptamine receptors" and "serotonin (5 hydroxytryptamine) M-receptor antagonists". Such compounds have been described as being useful inter alia in the treatment of migraine, emesis, anxiety, gastrointestinal disorders and as antipsychotics.

The compounds of the invention are tested for 5-HT3 antagonistic activity in the isolated right atrium of the rabbit heart based upon the method of Fozard J. R., Naunyn Schmiedeberg's Arch. Pharmacol., 1984, 326, 36–44. This procedure relies upon the ability of 5-HT to stimulate 5-HT3 receptors present on sympathetic nerve terminals in the heart, causing release of noradrenaline which evokes an increase in the spontaneous rate of beating. The antagonist potency is expressed as -log $IC_{50}$ (where $IC_{50}$ is the concentration of antagonist which reduces the chronotropic response to $10^{-5}M$ 5-HT by 50%).

When tested by this procedure 3 dimethylamino-1-[[(1H)-indol-3-yl]carbonyl]piperidine and 3-dimethylamino-1 [[(1H)-indazol 3-yl]carbonyl]piperidine representative compounds of this invention, had -log $IC_{50}$ values of 7.7 and 8.1 respectively.

Any suitable carrier known in the art can be used to prepare the pharmaceutical composition of the present invention. In such a composition, the carrier is generally a solid or liquid or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredients, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

The compounds of the invention can also be administered by the nasal route. When formulated for nasal administration the compositions may comprise the active compound in a liquid carrier; such compositions may be administered for example in the form of a spray or as drops. The compositions may be contained in a nasal applicator.

Preferably the pharmaceutical composition is in unit dosage form, e.g. as tablets or capsules. In such form, the composition is sub-divided in unit dose containing appropriate quantities of the active ingredient; the unit dosage form can be packaged composition, for example packeted powders, vials, ampoules, prefilled syringes or sachets containing liquids. The unit dosage form can be, for example, a capsule or tablet itself, or it can be the appropriate number of any such compositions in package form.

The quantity of the active ingredient in unit dose of composition may be varied or adjusted from 0.5 mg or less to 750 mg or more, according to the particular need and the activity of the active ingredient.

The invention also includes the compounds in the absence of the carrier where the compounds are in unit dosage form.

The following Examples illustrate the invention.

EXAMPLE 1

3-Dimethylamino-1-[[(1H)-indol 3 yl]carbonyl]piperidine

A mixture of 3-dimethylaminopiperidine dihydrochloride (1.8 g, 0.01 mol), N-methylmorpholine (2.5 g) and dichloromethane (50 ml) was stirred at ambient temperature for 1.5 h. Indole-3-carboxylic acid (1.92 g, 0.012 mol) was added, followed by dicyclohexylcarbodiimide (2.5 g) and the mixture stirred for 24 h. The mixture was filtered, the filtrate was washed thrice with 1M hydrochloric acid, the acid washings were combined, basified with ammonia and extracted with chloroform. The chloroform extract was dried and evaporated to yield the product base 1.6 g. The base was dissolved in isopropyl alcohol (20ml), acidified with maleic acid (0.72 g, 5% excess) and diluted with ether (10 ml). On standing the maleate salt crystallised and was collected by filtration, 1.04 g, mp 139-141.

EXAMPLE 2

3-Dimethylamino-1-[[1-methyl-(1H)-indol 3-yl]carbonyl]piperidine

A mixture of 3 dimethylaminopiperidine dihydrochloride (18 g; 0.01 mol), triethylamine (2.5 g) and dichloromethane (50 ml) was stirred for 15 min. 1-Methylindole-3-carboxylic acid (2.1 g, 0.012 mol) was then added, followed by dicyclohexylcarbodiimide (2 5 g). The mixture was stirred for 48h, filtered and extracted with 1M hydrochloric acid (20+10+10 ml). The acid extracts were basified with ammonia and back extracted to chloroform. The chloroform extract was dried, evaporated and the residue dissolved in IPA (25 ml), then acidified with ethanolic hydrogen chloride to precipitate the hydrochloride 2.55 g, mp 250-251° C.

EXAMPLE 3

3-Dimethylamino-1-(3,5-dichlorobenzoyl)piperidine

A mixture of 3 dimethylaminopiperidine dihydrochloride (0 9 g, 0.005 mol), triethylamine (1.5 g, 0.015 mol) and dichloromethane (20 ml) was stirred for 15 min. 3,5-Dichlorobenzoylchloride (1.05 g, 0.005 mol) was then added and stirring continued for a further 2 h. The solution was then washed with aqueous sodium carbonate solution, dried and evaporated. The residue was dissolved in isopropyl alcohol (15 ml) and acidified with ethanolic hydrogen chloride to precipitate the crystalline hydrochloride 1.3 g, mp 242-244° C.

EXAMPLE 4

3-Dimethylamino-1-[[(1H)-indazol 3 yl]carbonyl]piperidine

Dicyclohexycarbodiimide (1.25 g) was added to a stirred solution of 3-dimethylaminopiperidine dihydrochloride (1 g, 5 mmol), indazole3-carboxylic acid (1.05 g, 6 mmol) and triethylamine (1.25 g) in dichloromethane (25 ml). The mixture was stirred for 48 h, filtered and the filtrate extracted with 1M hydrochloric acid. The acid extracts were combined, washed with a little dichloromethane then basified with ammonia solution and back-extracted into chloroform. The extract was dried and evaporated. The residue was chromotographed on silica using methanol-methyl acetate (1:9) as eluent to give the product which was crystallised from a low volume of ethyl acetate to give the product (0.165 g) mp 141-142° C.

EXAMPLE 5

1-(4-Amino-5-chloro-2-methoxybenzoyl)-3-dimethylaminopiperidine

Triethylamine (4 ml, 2.9 g) was added to a stirred suspension of 3-(dimethyl)aminopiperidine dihydrochloride (2.21 g) in dichloromethane (50 ml). 4-Amino 5 chloro-2-methoxybenzoic acid (2.02 g) and dichlohexylcarbodiimide (2.06 g) were added and the solution was stirred at room temperature for 40 h. The mixture was filtered and the filtrate was concentrated in vacuo. Water (50 ml) and 2N aqueous hydrochloric acid (50 ml) were added and the mixture was extracted with ethyl acetate (2×50 ml). The aquous phase was basified at 0° C. with 2M NaOH (100 ml) and was extracted with ethyl acetate (3×100 ml). The extracts were dried ($Na_2SO_4$) and concentrated in vacuo to give a white foam (2.17 g) which was triturated with ether (2×50 ml). The solution was concentrated in vacuo to give the crude product (1.87 g). The product was dissolved in ethyl acetate (100 ml) and the solution was acidified with ethereal hydrogen chloride (5 ml). The product was filtered off and recrystallised from methanol/ethyl acetate to give the title compound as the hydrochloride, three quarters hydrate (1.30 g) mp 219-227° C.

I claim:

1. A piperidine derivative of formula

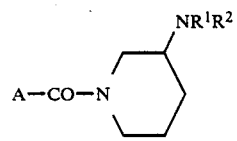 (I)

or a pharmaceutically acceptable acid addition salt thereof, wherein A represents an aromatic radical of the formula

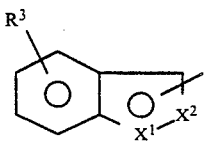

wherein
- $R^3$ is hydrogen, $(C_{1-4})$alkyl, $(C_{1-4})$ alkoxy or halogen;
- $X^1$—$X^2$ represents $NR^4$—CH, $CH_2$—N, $NR^4$—N, CH-$NR^4$ or N—$NR^4$, where $R^4$ is hydrogen, $(C_{1-4})$alkyl, phenyl or phenyl$(C_{1-4})$alkyl; and
- $R^1$ and $R^2$ are independently hydrogen, $(C_{1-4})$alkyl or $(C_{1-4})$alkylphenyl or $R^1$ and $R^2$ together with the nitrogen atom to which they are attached represent pyrrolidino or piperidino.

2. A compound as claimed in claim 1 wherein $X^1$—$X^2$ is $NR^4$—CH or $NR^4$—N.

3. A compound as claimed in claim 2 wherein $R^4$ is hydrogen or $(C_{1-4})$alkyl.

4. A compound as claimed in claim 2 wherein $R^3$ is hydrogen.

5. A compound as claimed in claim 1 which is 3-dimethylamino-1-[[(1H)-indol-3-yl]carbonyl]piperidine or a pharmaceutically acceptable acid addition salt thereof.

6. A compound as claimed in claim 1 which is 3-dimethylamino-1-[[1-methyl-(1H)-indol-3-yl]carbonyl]piperidine or a pharmaceutically acceptable acid addition salt thereof.

7. A compound as claimed in claim 1 which is 3-dimethylamino-1-[[(1H)-indazol-3-yl]carbonyl]piperidine or a pharmaceutically acceptable acid addition salt thereof.

8. A pharmaceutical composition comprising a pharmaceutically effective amount of a piperidine derivative as defined in claim 1, or a pharmaceutically acceptable acid addition salt thereof, in combination with a pharmaceutically acceptable carrier.

9. A pharmaceutical composition as claimed in claim 8 in the form of a tablet or capsule or in the form of a spray or as drops for nasal administration.

10. A method for antagonizing 5-HT$_3$ receptors in a mammal, which comprises administering to a mammal in need thereof an amount effective to antagonize 5-HT$_3$ receptors of a compound of formula I

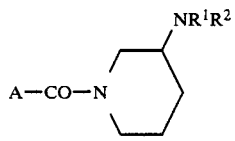

or a pharmaceutically acceptable acid addition salt thereof, wherein A represents an aromatic radical of the formula

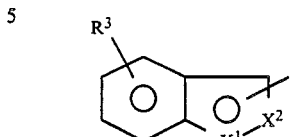

wherein
- $R^3$ is hydrogen, $(C_{1-4})$alkyl, $(C_{1-4})$ alkoxy or halogen;
- $X^1$—$X^2$ represents $NR^4$—CH, $CH_2$—N, $NR^4$—N, CH—$NR^4$ or N—$NR^4$, where $R^4$ is hydrogen, $(C_{1-4})$alkyl, phenyl or phenyl$(C_{1-4})$alkyl; and
- $R^1$ and $R^2$ are independently hydrogen, $(C_{1-4})$alkyl or $(C_{1-4})$alkylphenyl or $R^1$ and $R^2$ together with the nitrogen atom to which they are attached represent pyrrolidino or piperidino.

11. A method of treating migraine, emesis, anxiety, gastrointestinal disorders or psychotic disorders in a mammal, comprising administering to a mammal in need thereof an amount effective to alleviate such condition of a compound of Formula I

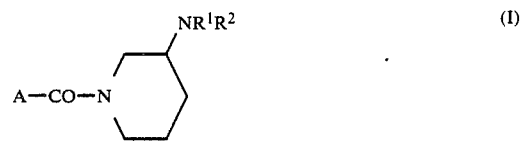

or a pharmaceutically acceptable acid addition salt thereof, wherein A represents an aromatic radical of the formula

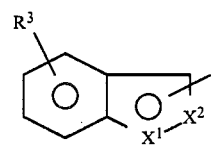

wherein
- $R^3$ is hydrogen, $(C_{1-4})$alkyl, $(C_{1-4})$ alkoxy or halogen;
- $X^1$—$X^2$ represents $NR^4$—CH, $CH_2$—N, $NR^4$—N, CH—$NR^4$ or N—$NR^4$, where $R^4$ is hydrogen, $(C_{1-4})$alkyl, phenyl or phenyl$(C_{1-4})$alkyl; and
- $R^1$ and $R^2$ are independently hydrogen, $(C_{1-4})$alkyl or $(C_{1-4})$alkylphenyl or $R^1$ and $R^2$ together with the nitrogen atom to which they are attached represent pyrrolidino or piperidino.

* * * * *